United States Patent [19]

Stein

[11] 3,968,202

[45] July 6, 1976

[54] TETANUS ANTIGEN AND PROCESS FOR ITS MANUFACTURE

[75] Inventor: Philipp Stein, Marbach near Marburg an der Lahn, Germany

[73] Assignee: Behringwerke Aktiengesellschaft, Marburg an der Lahn, Germany

[22] Filed: Aug. 9, 1974

[21] Appl. No.: 496,187

[30] Foreign Application Priority Data

Aug. 13, 1973 Germany.............................. 2340911

[52] U.S. Cl. ................................................. 424/92
[51] Int. Cl.² ......................................... A61K 39/02
[58] Field of Search ...................................... 424/92

[56] References Cited

UNITED STATES PATENTS

| | | | |
|---|---|---|---|
| 2,224,591 | 12/1940 | Boyd et al............................. | 424/92 |
| 3,522,347 | 7/1970 | Ablondi et al........................ | 424/92 |
| 3,542,920 | 11/1970 | Schwick et al........................ | 424/92 |

*Primary Examiner*—Shep K. Rose
*Attorney, Agent, or Firm*—Curtis, Morris & Safford

[57] ABSTRACT

Tetanus antigen which contains a tetanus toxin inactivated with oxymethane sulfinate and a process for the manufacture of this tetanus antigen by the inactivation of a tetanus toxin which comprises treating the tetanus toxin with oxymethane sulfinate.

6 Claims, No Drawings

TETANUS ANTIGEN AND PROCESS FOR ITS MANUFACTURE

The present invention relates to a tetanus antigen and a process for its manufacture.

It also relates to its use as an immunogen in tetanus vaccines or as an antigen in diagnostics.

Methods have been described according to which the tetanus toxin is treated with reducing agents, which treatment is to lead to a cleavage into sub-units. However, this cleavage is difficult to reproduce and, moreover, the splitting products cannot yet be worked to a vaccine, but must be inactivated.

Attempts have been made to suppress the vaccination reactions and intolerances caused by tetanus vaccines, which may be due to aggregations resulting from formaldehyde inactivation, by treating the inactivated tetanus toxin, the so-called tetanus toxoid, with pepsin.

The present invention provides a process for the manufacture of a tetanus vaccine which comprises treating tetanus toxin for its inactivation with an alkali metal salt of oxymethane-sulfinic acid, optionally stabilizing it by means of an acylating agent, filtering in sterile state and optionally working up to a vaccine by means of an adjuvant. The tetanus toxin so treated can be used alone as a monovalent vaccine or with other immunogens in combination vaccines as well as an antigen in diagnostics.

The starting material to be used for the process of the invention is tetanus toxin which is obtained in known manner by cultivating tetanus bacilli and a subsequent isolation. The action of an alkali metal salt of oxymethane-sulfinic acid, preferably the sodium salt, causes an alteration of the sedimentation constant of the toxin.

Vaccines prepared from the tetanus toxin treated according to the invention, are well tolerated. Furthermore, they are especially suitable for being boostered. An advantage lies in the fact that the vaccine of the invention can be added in high concentration in the preparation of combination vaccines so that the other components are not undesirably diluted.

The oxymethane-sulfinate (OMS) used for treating the toxin, for example, is available in commerce as the sodium salt under the name of "Rongalit." It corresponds to the chemical formula $CH_2(OH)-SO_2Na$ and is also known under the name of formaldehyde-sulfoxylic acid-sodium salt and oxymethanesulfinic acid-Na-salt.

The OMS is advantageously used in a concentration of 0.005 mol/l to 5.0 mols/l, preferably 0.25 mol/l. The higher the concentration the more rapid the reaction to inactivate the tetanus toxin. It can be added to the tetanus toxin solution as a solid substance or in solution or in an especially careful manner by dialysis.

The pH chosen is between 5 and 11, preferably 8.5, and is adjusted by means of a buffer usually used in bio-chemistry, for example, a 0.1 molar solution of disodium-hydrogen phosphate and potassium dihydrogen phosphate. The higher the pH of the solution the more rapid the reaction to inactivate the toxin.

The temperature suitable for the process of the invention is within the range of 0°C to 40°C, preferably 4°C. The higher the temperature chosen the more rapid the reaction with the alkali metal salt of the oxymethane sulfinic acid.

The reaction period depends on the reaction conditions used. It is within the range of 1 hour to 36 days, and takes 12 days under the preferred conditions indicated above.

The end of the reaction can be determined by a toxicity test, for example, on mice and guinea pigs.

The freedom from toxin was tested on a total of 10 mice. The tetanus antigen diluted to 30 Lf/ml was incubated at 20°C for at least 10 minutes with decreasing concentrations of tetanus antitoxin (serum of a horse immunised with tetanus toxoid). 0.4 ml each of the antigen-antitoxin-mixture was injected subcutaneously into the groin of 2 mice each. Two animals were administered antigen not treated with antitoxin. The preparation is considered as non toxic when all mice survive until the fourth day.

The tolerance of the products of the invention was demonstrated by a skin test on a guinea pig and by an anaphylaxis test on the uterine horn of a guinea pig.

CUTANE SENSITIVITY TEST ON GUINEA PIGS

The preparations to be characterized were injected subcutaneously into 10 guinea pigs immunised with tetanus toxoid. The dimension of the reaction halo on the injection place was taken as a measure for the tolerance of the preparation to be tested.

ANAPHYLACTIC SENSITIVITY TEST ON THE UTERUS HORN OF THE GUINEA PIG

With each 5 guinea pigs immunised with tetanus toxoid the isolated uterus horns were tested for their sensitivity against the tetanus immunogen to be characterized, in undilute state and diluted in the ratio 1 : 5 and 1 : 25 in an organ bath. The contraction was registered on a kymograph. It was a measure for the anaphylactic reaction of the preparation to be tested. The ratio of the number of animals in which a contraction was measured to the number of animals used was indicated as the result. The contractility of the uterus horns was tested with oxytocin.

The immunogenicity of the products of the invention was proved in guinea pigs. For this purpose, 10 guinea pigs were immunised subcutaneously with 2 ml of tetanus immunogen diluted to 0.66 Lf/ml. After 4 weeks the animals were challenged with 20 dlm, i.e., 20 times the amount of the minimum lethal dose, of tetanus toxin. The animals surviving the 5th day after the intoxication were considered as being protected.

Under $L_f/ml$ = limes flocculationes there is to be understood the amount of antigen which flocks out an international unit (i.e.) of antiserum.

The process of the invention does not change the specific floculation behavior of the toxin with tetanus antitoxin.

The term dlm is the abbreviation for dosis letalis minima.

The stability of the inactivated toxin can be increased by adding acylating agents, which are, for example acid chlorides or acid anhydrides, for example, acetic acid anhydride, succinic acid anhydride, citraconic acid anhydride. The best stability is obtained with diketene. 20 to 2,000 mols of diketene are added to 1 mol of inactivated tetanus toxin (corresponding to 130,000 g of protein), preferably, 150 μmol of diketene are added to the reaction products of 1 μmol of tetanus toxin. The immunogenic action of the inactivated toxin is not altered by diketene.

The tetanus antigen of the invention can be used after corresponding dilution for the immunisation of animals, for the obtention of antitoxic sera and, after desalting in known manner by dialysis, ultrafiltration or by means of molecular sieves, preferably a fractionation on a molecular sieve column, such as an Sephadex G-100$^{(R)}$, as immunogen for tetanus vaccine for human beings. Vaccines so prepared can be injected in known manner after sterile filtration as fluid vaccine or provided with adjuvants, preferably aluminium hydroxide.

The preparation of the invention can also be used as antigen in serological diagnostics for the proof of tetanus antibodies, for example in the flocculation test.

The following examples illustrate the invention:

EXAMPLE 1

11.9 g of OMS were dissolved at 4°C in 10 μmols of tetanus toxin obtained in known manner (corresponding to 1.3 g of protein) with an activity of 1,600 Lf/ml, suspended in 400 ml of 0.1 molar phosphate buffer of pH 8.5. An OMS concentration of 0.25 mol was reached. The reaction mixture was allowed to stand for 12 days at 4°C.

The freedom of the product obtained from toxin was tested on 10 mice in total. The product diluted to 30 Lf/ml was incubated at 20°C for at least 10 minutes with decreasing concentrations of tetanus antitoxin (serum of an immunised horse). Each 0.4 ml of the toxin-antitoxin mixture was subcutaneously injected into the groin of 2 mice each. Two animals were administered antigen not treated with antitoxin. All mice survived until the 4th day which demonstrated that the preparation was no longer toxic.

The product was then diluted with 63.6 l of isotonic sodium chloride solution in the volumetric ratio of 1 : 60, that is 10 Lf/ml, and subjected to sterile filtration. This solution was a tetanus vaccine and could be used for immunisation against tetanus in human beings and animals.

A parallel mixture was diluted with 57.2 l of isotonic sodium chloride solution, subjected to sterile filtration and 6.40 l of 1 % aluminum hydroxide gel were added. This tetanus vaccine contained 10 Lf/ml and is also usable for immunisation against tetanus.

EXAMPLE 2

10 μmols of tetanus toxin (corresponding to 1.3 g of protein) having 16,000 Lf/ml in 40 ml of 0.1 molar phosphate buffer of pH 8.5 were dialysed at 4°C against 1 l of 0.25 molar OMS solution in 0.1 molar phosphate buffer of pH 8.5 for 48 hours. The tetanus toxin solution reached a rongalite concentration of 0.25 mol. The mixture was then allowed to stand for 12 days at 4°C.

The toxin freedom of the product was tested in a dilution to 30 Lf/ml on 10 mice. After 4 days, none of the mice showed any symptoms of tetanus.

The product (40 ml) was then diluted with 60 ml of 0.1 molar phosphate buffer of pH 8.5 and 0.5 ml of diketene was added three times at intervals of 30 minutes each. Two hours after the last addition of diketene the unreacted diketene was eliminated by dialysing against an isotonic sodium chloride solution. To obtain the end product the solution so obtained was diluted with isotonic sodium chloride solution to 10 Lf/ml and subjected to sterile filtration.

Each 10 ml of a product obtained in a parallel reaction under the same conditions were stored at 20°C for 3 months before and after the treatment. The following Lf/values were obtained:

|  | without diketene | with diketene |
| --- | --- | --- |
| product | 1,600 Lf/ml | 1,600 Lf/ml |
| after 3 months at 20°C | 100 Lf/ml | 1,600 Lf/ml |

The values obtained show that the activity dropped to 100 Lf/ml without diketene treatment whereas the preparation treated with diketene maintained its activity.

EXAMPLE 3

Tetanus toxin was split with OMS and then diketene was added according to example 2. The reaction product obtained was fractionated by means of gel filtration on a column with Sephadex G-100. Two adsorption peaks with a wave length of 280 nm were registered in the eluate.

Both fractions, the first of which contained about 2/3 and the second one about 1/3 of the toxin used, were separately worked up according to example 1 to yield vaccines.

The two products of the invention were tested for their tolerance. In the cutane test on guinea pigs both preparations showed reaction halos of 12 mm dimension on an average. A tetanus toxoid used for comparison tests showed a reaction halo of 15 mm.

The following values were measured in the anaphylaxis test:

|  | contraction at 0.1 ml | | |
| --- | --- | --- | --- |
|  | undiluted | 1:5 | 1:25 |
| tetanus toxoid inactivated with formaldehyde | 4/5 | 2/5 | 1/5 |
| fraction I antigen | 3/5 | 1/5 | 0/5 |
| fraction II antigen | 3/5 | 1/5 | 0/5 |

It could be demonstrated according to both determination methods that the products of the invention have an improved tolerance as compared with the tetanus toxoid obtained by inactivation with formaldehyde according to the prior art.

When being tested for immunogenicity on guinea pigs both fractions proved to be active.

EXAMPLE 4

A reaction carried out according to example 3, however, for a reaction period of 20 days, yielded the two fractions in a quantitative ratio of 1 : 1.

EXAMPLE 5

The tetanus antigen obtained according to example 2 which was diluted with an isotonic sodium chloride solution to 875 Lf/ml was used for preparing combination vaccines against tetanus, diphtheria and pertussis as well as against tetanus, diphtheria, pertussis, measles and poliomyelitis of the following composition:

6.2 ml of tetanus antigen (875 Lf/ml)
5.0 ml of diphtheria toxoid (3,000 Lf/ml)
80.0 ml of germs of Bordetella pertussis
 (300 × 10$^9$ K/ml)

200 ml of a 1 % aluminum hydroxide gel were added to the mixture which had been filled up with isotonic sodium chloride solution to 800 ml.

6.2 ml of tetanus antigen (875 Lf/ml)
5.0 ml of diphtheria toxoid (3,000 Lf/ml)

80.0 ml of germs of Bordetella pertussis
   ($300 \times 10^9$ K/ml)
200.0 ml of measles viruses, strain No. 1677,
   Enders (5000HAE/ml)
200.0 ml of viruses of poliomyelitis I,II,III,
   each $5 \times 10^7 GKID_{50}$/ml 200 ml of a 1 % aluminum hydroxide gel were added to the mixture which had been filled up to 800 ml with isotonic sodium chloride solution.

To test the activity of the tetanus antigen of the invention in the vaccines, 50 guinea pigs were immunised with 2 ml of the vaccine and after 4 weeks challenged with 20 dlm of tetanus toxin. To test the activity of the diphtheria toxoid also 50 guinea pigs were immunised with 2 ml of the vaccine, and for the intoxication effected after 4 weeks 16 dlm of diphtheria toxin were used. The activity of the pertussis component was tested on $3 \times 18$ mice which were immunised with decreasing doses of the vaccine and challenged with 100 $dl_{50}$ by the intracerebral route. The potency of the measles viruses was determined by hemagglutination, that of the poliomyelitis viruses by their tissue culture infectiousness. The determinations were made each time in comparison with a reference preparation. The potencies measured in the tests corresponded to the potencies required in the prescriptions issued by the National Institutes of Health.

What is claimed is:

1. A method for making a tetanus antigen by the inactivation of a tetanus toxin, which comprises treating a solution of tetanus toxin with 0.005 to 5.0 mols per liter of oxymethane sulfinate at a pH between 5 and 11 and at a temperature between 0° and 40°C. until the toxicity of the tetanus toxin has disappeared.

2. The method of claim 1, wherein the tetanus antigen obtained is subsequently treated with an acylating agent selected from the group consisting of acid chlorides and acid anhydrides, whereby its immunogenicity is not altered.

3. The product obtained by the method of claim 1.

4. The product obtained by the method of claim 2.

5. An immunizing composition containing an effective amount of the product of claim 1.

6. An immunizing composition containing an effective amount of the product of claim 2.

* * * * *